US009636267B2

(12) United States Patent
Ackerman et al.

(10) Patent No.: US 9,636,267 B2
(45) Date of Patent: *May 2, 2017

(54) SUPPORT SURFACE SYSTEM FOR SECURING OBJECTS

(71) Applicant: Nichols Therapy Systems, LLC, Sabetha, KS (US)

(72) Inventors: Galen Ralph Ackerman, Sabetha, KS (US); Jarrod L Nichols, Manhattan, KS (US)

(73) Assignee: Nichols Therapy Systems, LLC, Manhattan, KS (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/714,441

(22) Filed: May 18, 2015

(65) Prior Publication Data
US 2015/0245966 A1    Sep. 3, 2015

Related U.S. Application Data

(63) Continuation of application No. 13/749,306, filed on Jan. 24, 2013, now Pat. No. 9,060,907.
(Continued)

(51) Int. Cl.
*A61G 7/05* (2006.01)
*A61G 13/10* (2006.01)

(52) U.S. Cl.
CPC .......... *A61G 7/0526* (2013.01); *A61G 13/10* (2013.01)

(58) Field of Classification Search
CPC .... A61G 7/0504; A61G 7/0526; A61G 13/10; A61G 7/05; A61F 5/3776; A61F 5/3784
See application file for complete search history.

(56) References Cited

U.S. PATENT DOCUMENTS

| 3,343,864 A | 9/1967 | Baer |
| 2,981,528 A | 9/1976 | Andorf |

(Continued)

FOREIGN PATENT DOCUMENTS

WO    WO9015697    12/1990

OTHER PUBLICATIONS

Authors: Covidien Title: Operating Room Positioning Products Title of the item: Catalog.
(Continued)

*Primary Examiner* — David E Sosnowski
*Assistant Examiner* — Eric Kurilla
(74) *Attorney, Agent, or Firm* — Coughlin Law Office; Daniel J. Coughlin

(57) ABSTRACT

An apparatus has conforming arms each respectively attached to a support surface in a pattern for cooperatively receiving an object. Actuators respectively position the plurality of conforming arms between a disengaged state to receive the object and an engaged state to contact the object at a respective contact area to immobilize the object. A control system selectively controls each of the actuators to cause the respective one of the conforming arms to curve inwardly toward the object to cooperatively exert a grasping force upon the object such that only a fraction of total force required to immobilize the object is applied to the object by each individual conforming arm. A selected grasping force of a selected one of the conforming arms corresponds to a relative fragility of the respective contact area.

19 Claims, 11 Drawing Sheets

Related U.S. Application Data

(60) Provisional application No. 61/623,081, filed on Apr. 12, 2012.

(56) References Cited

U.S. PATENT DOCUMENTS

| | | | |
|---|---|---|---|
| 4,815,782 A | 3/1989 | Craig | |
| 4,976,191 A | 12/1990 | Suzumori | |
| 5,060,324 A | 10/1991 | Marinberg | |
| 5,079,999 A | 1/1992 | Negishi | |
| 5,083,498 A | 1/1992 | Sato | |
| 5,158,005 A | 10/1992 | Negishi | |
| 5,190,055 A * | 3/1993 | O'Connor | A61F 5/3769 128/869 |
| 5,201,262 A | 4/1993 | Negishi | |
| 5,239,716 A | 8/1993 | Fisk | |
| 5,251,538 A | 10/1993 | Smith | |
| 5,385,080 A | 1/1995 | Suzumori | |
| 5,398,983 A | 3/1995 | Ahrens | |
| 5,425,381 A * | 6/1995 | Peterson | A61G 15/105 128/876 |
| 5,556,169 A * | 9/1996 | Parrish | A42B 3/121 297/452.28 |
| 5,568,957 A | 10/1996 | Haugs | |
| 5,833,291 A | 11/1998 | Haugs | |
| 5,860,176 A * | 1/1999 | Norberg | A61G 1/00 128/870 |
| 6,230,342 B1 | 5/2001 | Haugs | |
| 6,308,353 B1 | 10/2001 | Van Steenburg | |
| 6,484,601 B1 | 11/2002 | Arrichiello | |
| 6,934,987 B2 | 8/2005 | Newkirk | |
| 7,086,322 B2 | 8/2006 | Schulz | |
| 7,234,180 B2 | 6/2007 | Horton | |
| 7,331,273 B2 | 2/2008 | Kerekes | |
| 7,669,262 B2 | 3/2010 | Skripps | |
| 8,187,279 B2 * | 5/2012 | Livorsi | A61B 17/154 600/233 |
| 8,234,730 B2 | 8/2012 | Skripps | |
| 8,236,057 B2 | 8/2012 | Wirtel, III | |
| 8,240,310 B2 * | 8/2012 | Soung | A61B 6/0428 128/845 |
| 2004/0244114 A1 * | 12/2004 | Robinette | A61F 5/3792 5/626 |
| 2005/0126578 A1 | 6/2005 | Garrison | |
| 2007/0062364 A1 | 3/2007 | Luchsinger | |
| 2008/0301878 A1 | 12/2008 | Elhabashy | |
| 2010/0095455 A1 | 4/2010 | Brinkerhoff | |
| 2010/0192300 A1 | 8/2010 | Tannoury | |
| 2011/0047706 A1 | 3/2011 | Hiebert | |
| 2012/0043777 A1 | 2/2012 | Maffeis | |

OTHER PUBLICATIONS

Authors: Steris Title: Interoperative Patient Positioning: It's More Than Just Comfort Title of the Item: Magazine.

Authors: Stacey L. Gorniak, Vladimir M. Zatsiorsky, and Mark L. Latash Title: Manipulation of a fragile object Title of the item: Journal Article.

Authors: Akihiko Yagi, Kiyoshi Matsumiya, Ren Masamune, Hongen Liao, and Takeyoshi Dohi Title: Rigid-Flexible Outer Sheath Model Using Slider Linkage Locking Mechanism and Air Pressure for Endoscopic Surgery Title of Item: Journal Article pp. 503-510, R. Larsen, M. Nielsen, and J. Sporring (Eds.):MICCAI 2006, LMCS 4190 pp. 503-510, 2006. (C) Springer-Verlag Berlin Heidelburg 2006.

* cited by examiner

SUPPORT SURFACE SYSTEM FOR SECURING OBJECTS

CROSS-REFERENCE TO RELATED APPLICATION

This application is a continuation of U.S. patent application Ser. No. 13/749,306, filed 24 Jan. 2013, which is an application claiming priority of U.S. provisional patent application 61/623,081 filed on 12 Apr. 2012. The above-identified applications are hereby incorporated herein by reference in their entirety.

FIELD

This disclosure generally relates to a support surface that dynamically conforms to the shape of a partially fragile object to stabilize the object.

BACKGROUND

Securing a fragile object in a particular position for manipulation or transportation has application in many fields. Specifically in the medical field, the fragile body of a surgical patient must be maintained in a proper position for the duration of many surgical procedures. This typically involves securing the patient to a flat operating table. The patient's position is then supported through the use of disposable padding such as foam "egg crate" material in a manner intended to minimize pressure points. Efforts to secure the extremities usually involve tape, straps, sheets, blankets, towels, and/or additional egg crate. Frequently, the patient is secured to the operating table by her own weight.

Once the anesthetized patient is positioned and gravitationally secured, they are normally fully draped, obscuring all further direct visual observation of the positioning mechanism. Certain positions and procedures carry increased risk for particular positioning difficulties and inherently carry risk for specific injuries to patients. For example, while placing a gynecology patient's legs in stirrups attached to the operating table, care must be taken to properly position her legs so as not to create too much pressure on the large nerves that supply the lower limbs to prevent permanent paralysis of certain muscle groups in her legs. The presence of view-impairing patient draping greatly increases the risk that the surgical team will be unaware of a patient body or limb shift at any time once the surgical procedure has begun.

During surgeries, the surgeon will often adjust the position of the patient support surface of the operating table to give the surgeon better access to the treatment area by shifting away pressure from the patient's internal organs. Positions such as Trendelenburg or Reverse Trendelenburg are common and essentially tilt the head of the bed toward the ground and vice versa, respectively.

These positions typically result in a dramatic change in the gravitational forces that are keeping the patient in position on the table. In surgery where steep Trendelenburg is required, such as laparoscopy and even robotic surgery, patients can slide toward the head of the bed. This sliding negates the earlier time investment in positioning precautions and can result in injury to the patient. Generally, shoulder pads cannot be used due to the increased risk of nervous injury in the upper extremities.

If the patient's overall body position shifts during a robotic surgery, the robotic surgery machine does not have the capacity to shift with the patient. Any shift in the patient's body during robotic surgery puts the patient at risk of injury to the point of surgery as well as any extremities that could be contacted by the robotic arm.

A more modern solution to positioning patients is disclosed in U.S. Pat. No. 6,308,353 to Van Steenburg, which discloses a patient support system with a series of vacuum-bags filled with beads. In a relaxed state, the vacuum-bags are flexibly positioned around the patient's body. The air is then removed from the bags, leaving a rigid, solid support wall that surrounds the patient's body.

Many non-surgical medical applications require the patient to be immobilized, such as therapeutic systems, patient imaging, and post-operative recovery. Many therapy systems rely on significant strapping pressures to stabilize a patient. This can result in considerable discomfort and has potential to cause damage due to excessive pressure to certain locations. This can result in considerable discomfort and tissue trauma.

In patient imaging, the patient is often supine on a flat or nearly flat surface and may or may not be strapped or otherwise secured in place on that surface. If the unsecured patient cannot be convinced to remain still during the procedure (such as infants, small children, or the elderly with associated senility or other mental state altering condition), then the imaging resulting from the procedure may be compromised or even unusable.

Securely and rapidly grasping objects, especially those of irregular shape or fragile construction, has proven to be an obstacle to efficiency and profitability.

SUMMARY

In one aspect, the present disclosure provides an apparatus that has conforming arms each respectively attached to a support surface in a pattern for cooperatively receiving an object. Actuators respectively position the plurality of conforming arms between a disengaged state to receive the object and an engaged state to contact the object at a respective contact area to immobilize the object. A control system selectively controls each of the actuators to cause the respective one of the conforming arms to curve inwardly toward the object to cooperatively exert a grasping force upon the object such that only a fraction of total force required to immobilize the object is applied to the object by each individual conforming arm. A selected grasping force of a selected one of the conforming arms corresponds to a relative fragility of the respective contact area.

In another aspect, the present disclosure provides a method for securing an object that is composed of a less fragile area and a more fragile area by responding to a user input on a user interface to immobilize an object on a support surface by associating a relative fragility of a contact area of an object on the support surface with a corresponding conforming arm of more than one conforming arm attached to the support surface; and by selectively actuating the more than one conforming arm to inwardly curve in cooperative opposition to engage and immobilize the object. The selectively actuating creates a selected grasping force of a selected one of the more than one conforming arm that corresponds to a relative fragility of the respective contact area.

In an additional aspect, the present disclosure provides an apparatus for securing an object that is partially fragile, composed of less fragile areas and more fragile areas. A plurality of conforming arms each comprises a contacting surface and an actuating surface and each respectively is attachable to a support surface in a pattern for cooperatively receiving an object. A plurality of actuators respectively positions the plurality of conforming arms by selectively expanding and retracting the actuating surface to inwardly curve the contacting surface between a disengaged state to receive the object and an engaged state to contact the object at a respective contact area to immobilize the object. A control system dynamically controls each of the plurality of actuators to cause the respective one of the plurality of conforming arms to curve inwardly toward the object to cooperatively exert a grasping force upon the object such that the object is immobilized and the more fragile areas are not damaged.

These and other features are explained more fully in the embodiments illustrated below. It should be understood that in general the features of one embodiment also may be used in combination with features of another embodiment and that the embodiments are not intended to limit the scope of the invention.

BRIEF DESCRIPTION OF DRAWINGS

Aspects are illustrated by way of example, and not by way of limitation, in the accompanying drawings, wherein.

DETAILED DESCRIPTION

Figure 1:
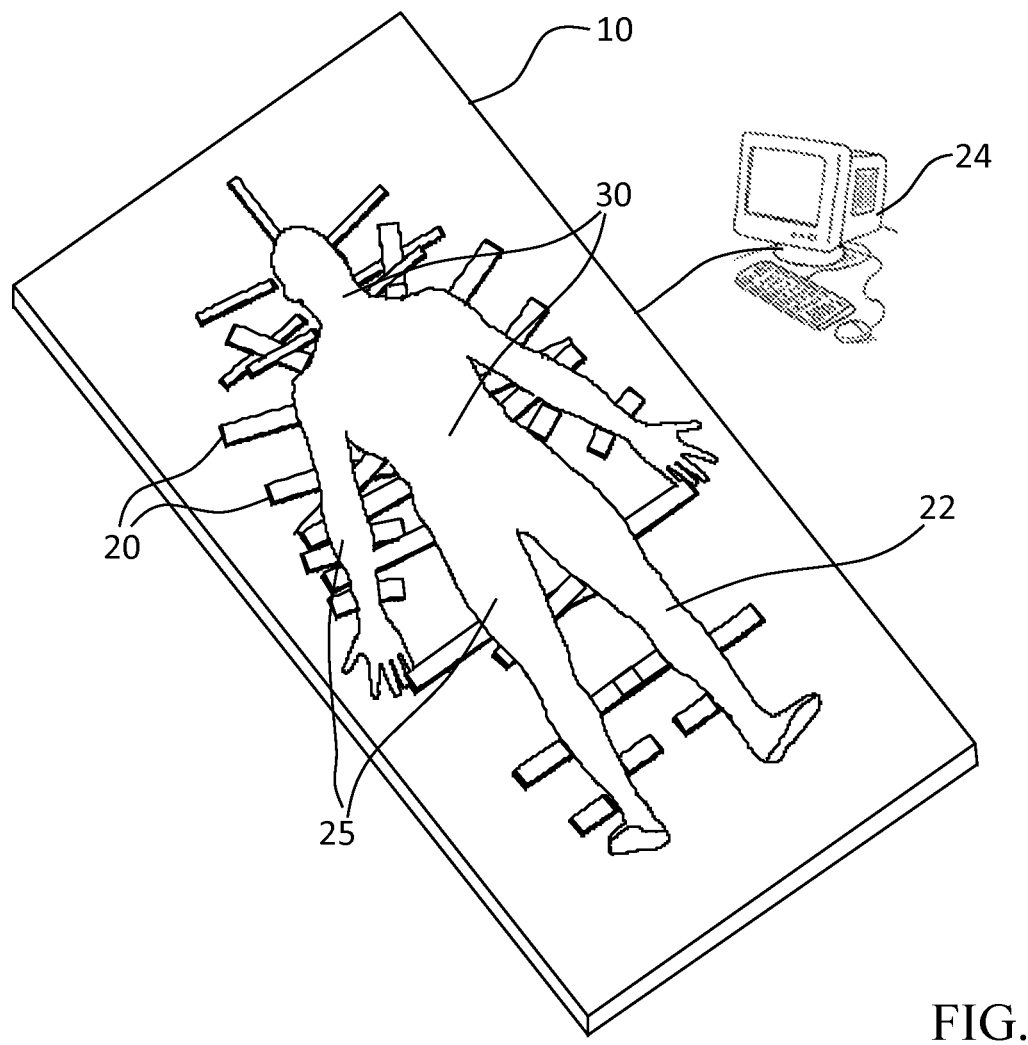
FIG. 1 is a perspective view of the unengaged support system.

The present innovation provides a prehensile support system that selectively distributes subjacent, lateral, and superjacent pressure through a series of conforming, bending arms that work together to secure and stabilize an object that is at least partially fragile.

In one aspect, an object support surface has two or more conforming arms. The conforming arms dynamically conform to the shape and contour of an object placed in contact with the face of the support surface. The conforming arms cooperate to distribute sufficient grasping or gripping force to immobilize the object without causing injury or other damage to the object. Immobilization of the object prevents the object from being unintentionally moved due to changes in gravitational or other forces that would otherwise cause the object to change position or move relative to the support surface. The support surface can engage the whole object or only a portion of the object. This is especially important for engaging partially fragile objects, where portions of the object are more fragile than others. For example, a standard light bulb is more fragile at the top glass portion and less fragile at the metallic screw band. Similarly, in a human body the chest, pelvis, legs, arms and skull are less fragile than the neck, groin, and abdomen.

For example, some features of the present disclosure may include an apparatus that provides:
  fast and gentle position stabilization especially for securing the position of objects that are partially fragile;
  a series of grasping and conforming arms that selectively apply distributed force around the perimeter of an object;
  decreased adverse outcomes associated with improper support and immobilization methods currently being used as standard of medical care and decreased time necessary to properly position and immobilize patients;
  individually controllable conforming segments capable of adapting to the wide range of body types, conformations, shapes, Body Mass Index (BMI) values, and body region vulnerabilities;
  a computerized or otherwise automated control system to control the application of the conforming and grasping force that results in safe, repeatable, predictable immobilization for a fragile object;
  a comfortable, safe, secure and quickly-engaged method of connecting a reduced functionality limb to an external control mechanism; and
  a self-sufficient system to provide object positioning coupled with one or more of the following: temperature regulation, support of extremities and spinal support, proper positioning to remove the risk of nervous injury.

Accordingly, one aspect of the disclosure includes an object support surface with two or more conforming arms. The conforming arms are capable of dynamically conforming to the shape and contour of an object placed in contact with the face of the surface. The conforming arms cooperate to distribute sufficient grasping or gripping force to immobilize the object without applying sufficient force to cause injury or other damage to the object. Immobilization of the object prevents the object from being unintentionally moved due to changes in gravitational or other forces that would otherwise cause the object to change position or move relative to the support surface. The support surface can engage the whole object or only a portion of the object. This is especially important for engaging partially fragile objects, where portions of the object are more fragile than others. For example, a standard light bulb is more fragile at the top glass portion than at the metallic screw band. Similarly, in a human body the chest, pelvis, legs, arms and skull are less fragile than the neck, groin, and abdomen.

In an unengaged state, the support surface is capable of receiving the object. When activated, the arms engage the object by curving towards the object. Each arm conforms to the contour of the object as the conforming arm continues to bend toward the object. The conforming arms cooperatively exert a grasping force on the object sufficient to maintain or intentionally change the position of the object. The conforming arms are engaged based on the relative fragility of the contact area between the respective conforming arm and the object. The relative fragility means the object has some areas that are more fragile and other areas that are less fragile. In one embodiment, the conforming arms can be selectively activated such that only the individual conforming arms that contact the object at a less fragile contact area are engaged. In another embodiment, the conforming arms exert a variable grasping or gripping force such that the grasping or gripping force of individual conforming arms is inversely proportional to the relative fragility of the respective contact area.

In another aspect of the invention, the object contact surface is made up of a flexible material. The thickness of the flexible material is determined by intended application and by the relative fragility of the object or body to be engaged. In one embodiment, the conforming arms have two surfaces. The first surface, the object contact surface, contacts the object and is made from a material that is flexible and compressible. In one embodiment, the object contact surface is stretched between two or more conforming arms to increase the surface area of contact between the object contact surface and the object. By engaging the object or patient with a contact surface of large surface area and relatively high surface friction, the combination of prehensile grasping, large contact area and high friction result in significant reduction in the object or patient's tendency to shift in relation to the contact surface. This is all accomplished with minimal gross pressure being applied to the overall object or patient.

The second surface, the actuator surface, is flexible or otherwise expandable and capable of creating a bending force that causes the entire conforming arm to bend toward the object. In another aspect of the invention, the dynamic conforming action is caused by either operator-generated or mechanically-generated force transmitted via cable, rope, strap or other linear actuator or force transmitter. The conforming action may be also be generated by fluid or other mechanical force energizing of one or more actuators in communication with the conforming arm.

In another aspect of the invention, the linear force is transferred to a bending, grasping force by the actuator surface having two edges, one edge that is hinged and the other edge that is unhinged. The linear force causes the actuator surface to expand at the unhinged edge and to bend at the hinged edge. In another embodiment, the actuating surface utilizes a bellows tube that has two edges, an expandable edge and a fixed length edge. The fluid or mechanical pressure causes the actuator surface to expand at the expandable edge and to bend about the fixed-length edge. Securing the fixed-length edge to a non-elastic object contact surface restricts the expandability of the bellows.

In another aspect of the invention, the conforming arms are integrated in a patient support surface that is generally flat and capable of being placed between the patient and a hospital bed or surgical table. In the non-engaged state, the conforming arms lay generally flat and provide a flat surface for laying a patient. In the activated state, the conforming arms curve toward the object to exert a grasping force on the patient's body.

In another aspect of the present disclosure, the individual conforming arms are arranged in a pre-determined orientation to best facilitate non-injurious engagement along the perimeter or outline of the object. For example, in a human body the chest, pelvis, legs, arms and skull are less fragile than the neck, groin, and abdomen. In order to grasp a human body, the conforming arms are positioned to engage the less fragile areas.

In another aspect of the present disclosure, the conforming arms are distributed around the perimeter of the object, including both fragile and non-fragile areas. A control system independently controls the activation of individual conforming arms. Control over individual actuators allows the support system to engage the object such that the conforming arms apply less pressure to the more fragile portion of the object. Alternatively, the control system can control groups or zones of multiple conforming arms, such as a group of conforming arms that engage the legs of a human body and another group that engages the arms of the body. The control system can also regulate the extent of grasping pressure applied to the fragile areas distinct from the non-fragile areas.

In another aspect of the present disclosure, the control system controls the activation of the individual conforming arms in order to alternate the pressure contact areas to reduce and prevent damage from prolonged pressure. In the engaged state, each conforming arm exerts a grasping force on the object. The control system can engage and disengage individual conforming arms to alternate the grasping force pressure on specific portions of the object. In the case of a human body, alternating the activation state of individual conforming arms can prevent trauma that can result from the prolonged grasping force.

In another aspect of the present disclosure, the object support system can maintain a desired object or patient core body temperature by pumping heating or cooling fluids within the object conforming arms. The contact of the conforming arms around the perimeter of the object will facilitate rapid heat transfer. The control system can monitor the temperature of the object and pump fluid for heating or cooling the object to maintain the desired temperature.

The present invention is capable of embodiment in many different forms. The drawings illustrate and the specification describes certain preferred embodiments of the invention. The disclosure of preferred embodiments is not intended to limit the principles of the present invention to the disclosed embodiments.

Referring now to the invention in more detail, in FIG. 1 there is shown an embodiment of the support surface 10. The support surface 10 includes a plurality of conforming arms 20. The conforming arms 20 are shown in an unengaged state to receive an object 22. A control system 24 controls the engagement of the conforming arms 20. The object 22, which is illustrated as a supine human body, has both less-fragile areas 25 and fragile areas 30.

In the unengaged state, the support surface 10 is capable of receiving the object 22. The unengaged conforming arms 20 lay generally flat, in-line with the support surface 10. This allows an object 22, such as a patient's body, to be easily placed on the support surface 10. The generally flat support surface 10 can accept a patient in the unengaged state similar to a traditional surgical bed surface, which allows for simple patient transfers to the support surface 10.

Figure 2:
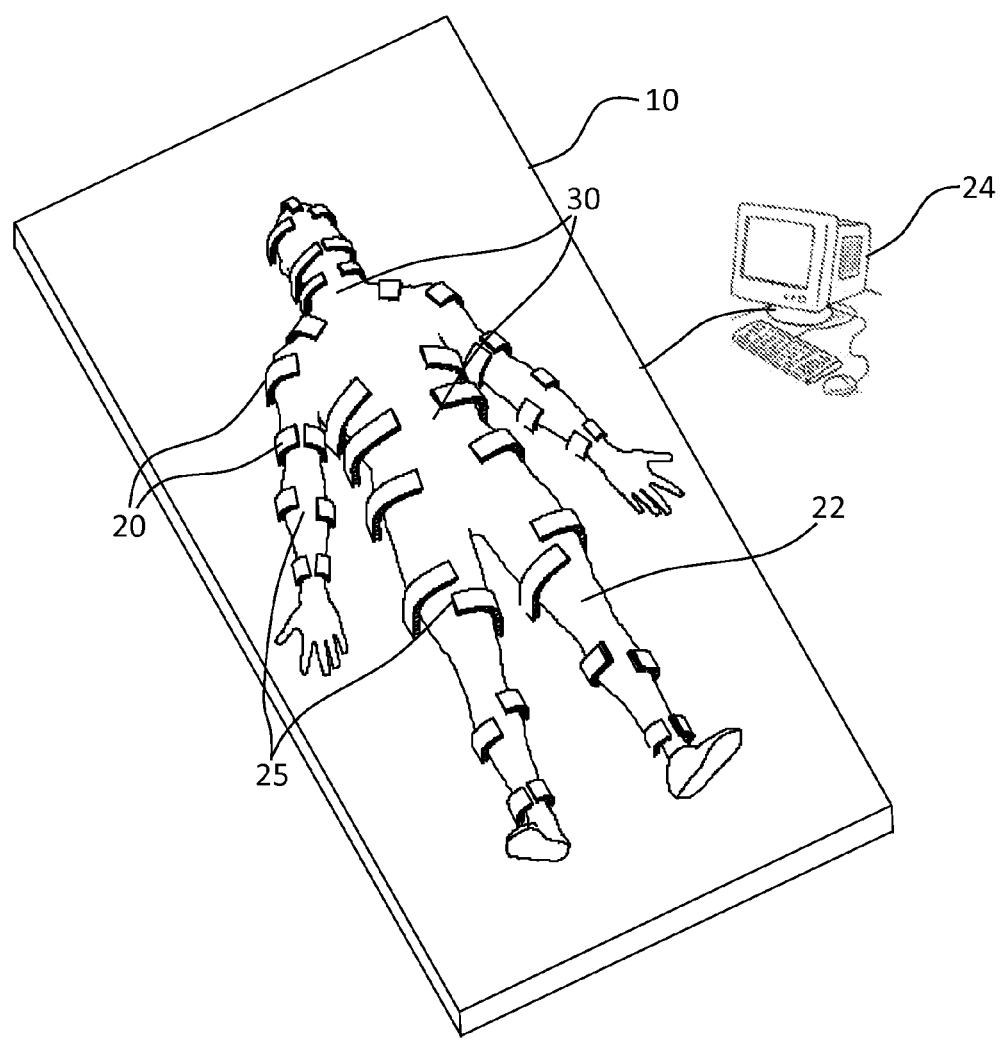
FIG. 2 is a perspective view of the engaged support system.

As shown in FIG. 2, the conforming arms 20 can be activated to engage the object 22. The conforming arms 20 engage the object 22 by curving towards the object 22. Each conforming arm 20 is capable of being positioned in a predetermined location around the perimeter of the object 22. One or more conforming arms 20 are positioned in opposition to at least one conforming arm 20, thereby allowing the support surface 10 to grasp the object 22. The conforming arm 20 exerts a grasping force on the object 22 to maintain or intentionally change the position of the object 22.

Figure 3:
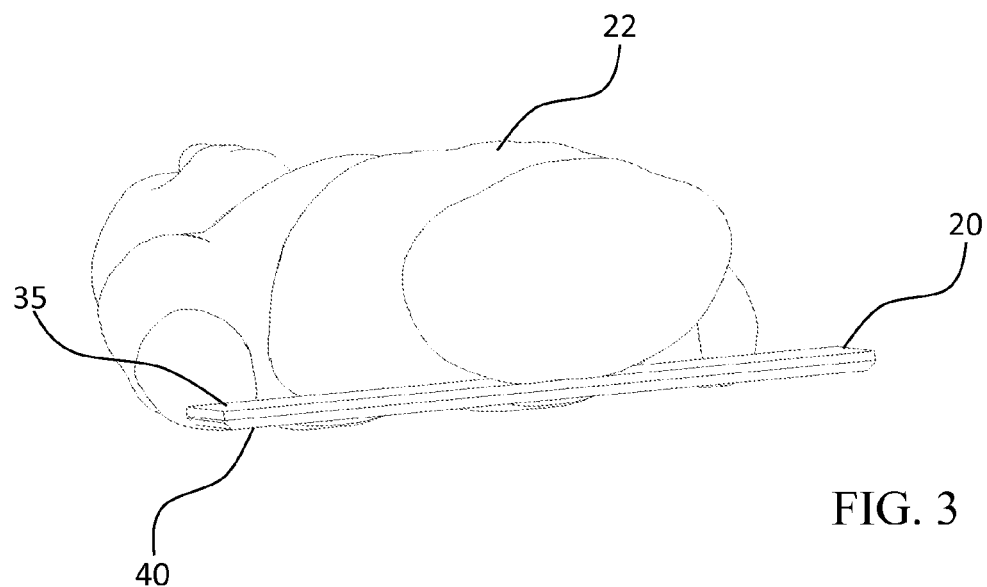
FIG. 3 is a cross-sectional view of the unengaged support system.
Figure 4:
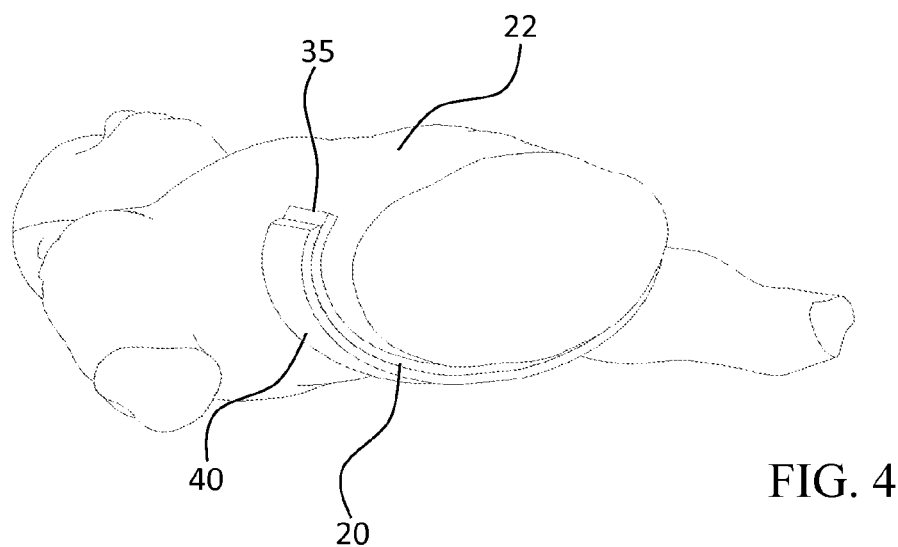
FIG. 4 is a cross-sectional view of the engaged support system.

As shown in FIG. 3, an individually depicted conforming arm 20 receives the object 22 in the unengaged state, where the conforming arm 20 is generally flat. Upon activation, as shown in FIG. 4, the conforming arm 20 curves inwardly towards the object. The conforming arm 20 conforms to the perimeter of the object regardless of the shape. In the illustrated embodiment, the conforming arm 20 has two surfaces. The first surface is an object contact surface 35. The second surface is an actuating surface 40. The two surfaces are in communication with each other, such that actuation of the actuating surface 40 causes the object contact surface 35 to bend. The object contact surface 35 engages to a contact area on the object 22 when engaged as depicted in FIG. 4.

The object contact surface 35 can be made of any material that is flexible, relatively high surface friction, compressible, and can safely contact the object. For use with the human body, the object contact surface 35 can be made of any flexible material that is currently in use in hospital bedding, surgical tables, or patient supporting materials. Furthermore, the thickness of the object contact surface 35 is variable depending on the intended application. For compressible materials, a thicker surface will allow greater conformity with the object's perimeter and allow greater dispersal of the grasping force.

In one embodiment, the placement of the conforming arms 20 corresponds to the general perimeter of the object 22. Referring again to FIG. 1, the support surface 10 is configured to receive a human body. Therefore the arrangement of the conforming arms 20 is predetermined to align with the perimeter outline of a generic human body, where conforming arms 20 are positioned to engage the head, neck, shoulders, arms, torso, pelvis, and legs. For engaging a human body, the arrangement of the conforming arms 20 could be positioned to only engage a specific region of the body, such as only the torso or only a single arm.

Furthermore, the individual conforming arms 20 can be arranged in a predetermined orientation to best facilitate non-injurious engagement along the perimeter of the object where a portion of the object is more fragile than another portion of the object. Again referring to engaging a human body, the chest, pelvis, legs, arms and skull are less fragile areas 25. The neck, groin, and abdomen are fragile areas 30. Therefore in one embodiment, the conforming arms 20 are placed around the perimeter of the human body in order to selectively engage the less fragile areas 25, such as the chest, pelvis, legs, arms, and skull.

In another embodiment, the conforming arms 20 are distributed around the perimeter of the object, including both fragile areas 30 and less fragile areas 25. A control system 24, as described below, independently controls the activation of individual conforming arms 20. This individual controls allows the support system to engage the object such that the conforming arms 20 apply less grasping pressure to the fragile areas 30 of the object. Alternatively, the control system can control groups or zones of multiple conforming arms 20, such as a group of conforming arms that engage the legs of a human body and another group that engages the arms of a human body. Adjusting the grasping or gripping force of each conforming arm 20 in correspondence with the relative fragility of the contact area 41 may be achieved by one or more of sizing respective conforming arms 20 for an amount of mechanical advantage that corresponds to the relative fragility, by selecting a power rating of each actuator (discussed below) to correspond to the relative fragility, or adjusting a commanded value of actuation by the control system 24 to correspond to the relative fragility.

Returning to FIGS. 3-4, the actuating surface 40 can be made of any material that causes the conforming arm to bend inwardly toward the object. The following embodiments can create a bending force for use in the actuating surface 40.

Figure 5:
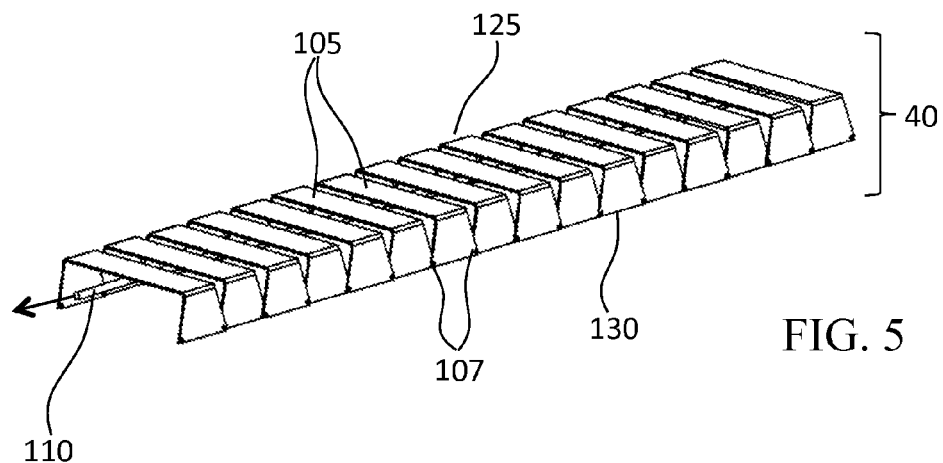
FIG. 5 is a perspective view of a refract-to-engage embodiment of the unengaged articulating surface of the conforming arm.
Figure 6:
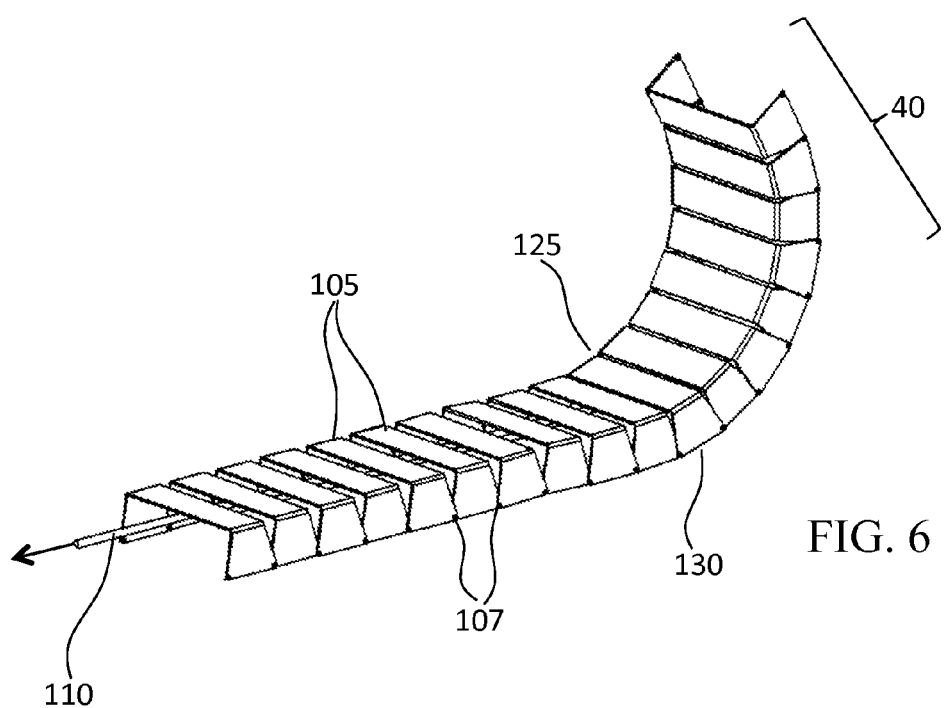
FIG. 6 is a perspective view of a retract-to-engage embodiment of the engaged articulating surface of the conforming arm.

In FIG. 5, there is shown the actuating surface 40 that is engaged by retracting an actuator 110, thus a refract-to-engage actuator. The actuating surface 40 is made of a series of segments 105 that are connected by a series of hinges 107. The actuating surface 40 has a non-hinged edge 125 and a hinged edge 130. The actuator 110 passes through or otherwise maintains slidable contact with each individual segment 105. When the actuator 110 is retracted, the series of segments begins to bend at the series of hinges 107. The pressure created by the actuator 110 causes the series of segments 105 to bend inwardly toward the object, as shown in FIG. 6. Refracting the actuator 110 causes the non-hinged edge 125 of each individual segment to pivot or bend toward the immediately adjacent segments 105.

As the actuator 110 continues to be retracted, the actuating surface 40 will cause the conforming arm 20 to conform to the object and begin to exert a grasping force against the perimeter of the object 22. This curving action causes the conforming arm 20 to conform to any shape of object 22 that is positioned on the support surface 10 with a grasping force directly related to the amount of retracting force applied to the actuator 110. The series of hinges 107 can be any movable joint, flexing connection, or other mechanism that links the individual segments 105 and allows the segments to pivot relative to the adjacent segments 105.

Figure 7:
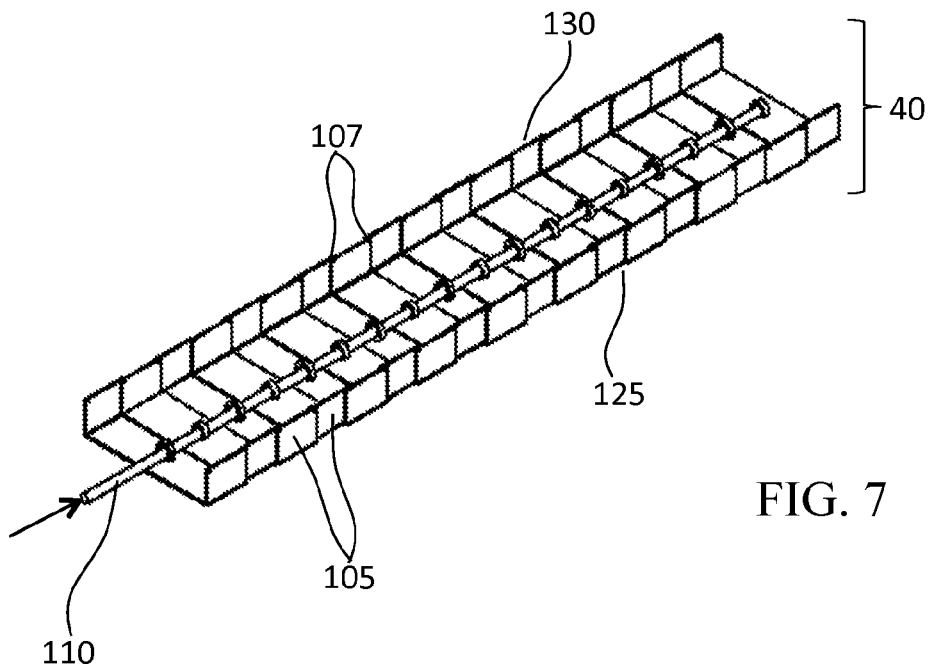
FIG. 7 is a perspective view of an extend-to-engage embodiment of the unengaged articulating surface of the conforming arm.
Figure 8:
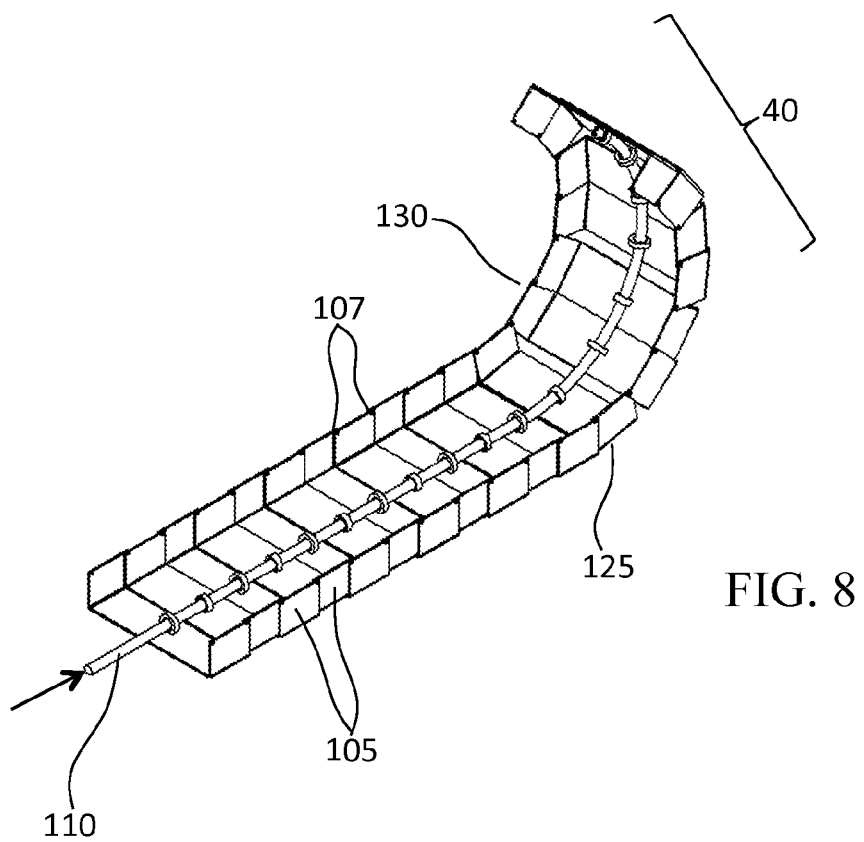
FIG. 8 is a perspective view of an extend-to-engage embodiment of the engaged articulating surface of the conforming arm.

In FIG. 7, there is shown the actuating surface 40 that is engaged by extending an actuator 110, thus an extend-to-engage actuator. The actuating surface 40 is made up of a series of segments 105 that are connected by a series of hinges 107. The actuator 110 passes through or is otherwise maintained in slidable contact with each individual segment 105. When the actuator 110 is extended, the series of segments begins to bend at the series of hinges 107. The pressure created by the actuator 110 causes the series of segments 105 to bend inwardly toward the object, as shown in FIG. 8. Extending the actuator 110 causes the non-hinged edge 125 of each individual segment to pivot or bend away from the immediately adjacent segment.

As the actuator 110 continues to extend, the actuating surface 40 will cause the conforming arm 20 to conform to the object 22 and begin to exert a grasping force against the perimeter of the object 22. This curving action causes the conforming arm 20 to conform to any shape of object 22 that is positioned on the support surface 10 with a grasping force directly related to the amount of extending force applied to the actuator 110. The series of hinges 107 can be any movable joint, flexing connection, or other mechanism that links the individual segments 105 and allows the segments to pivot relative to the adjacent segments.

Figure 9:
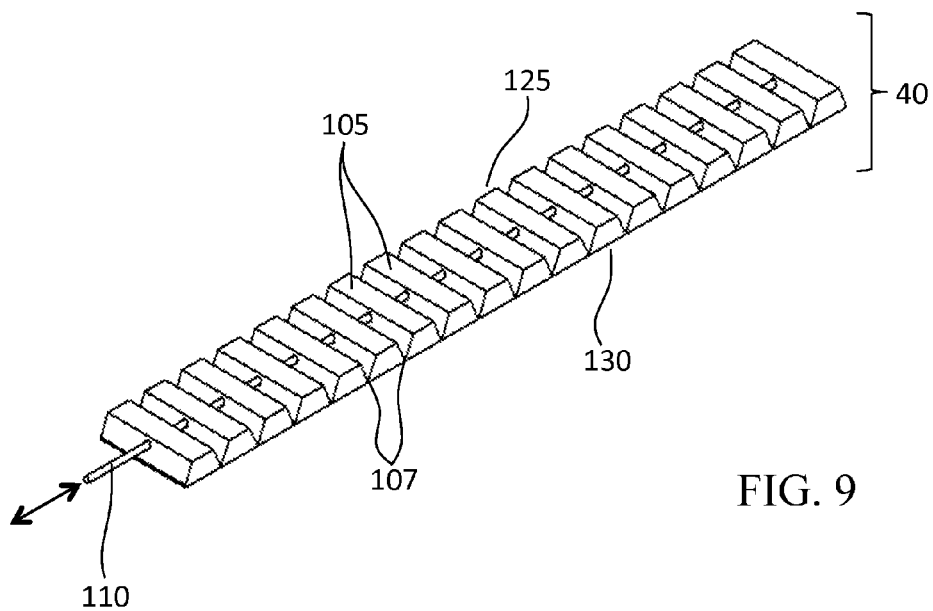
FIG. 9 is a perspective view of an extend-or-retract-to-engage embodiment of the unengaged articulating surface of the conforming arm.
Figure 10:
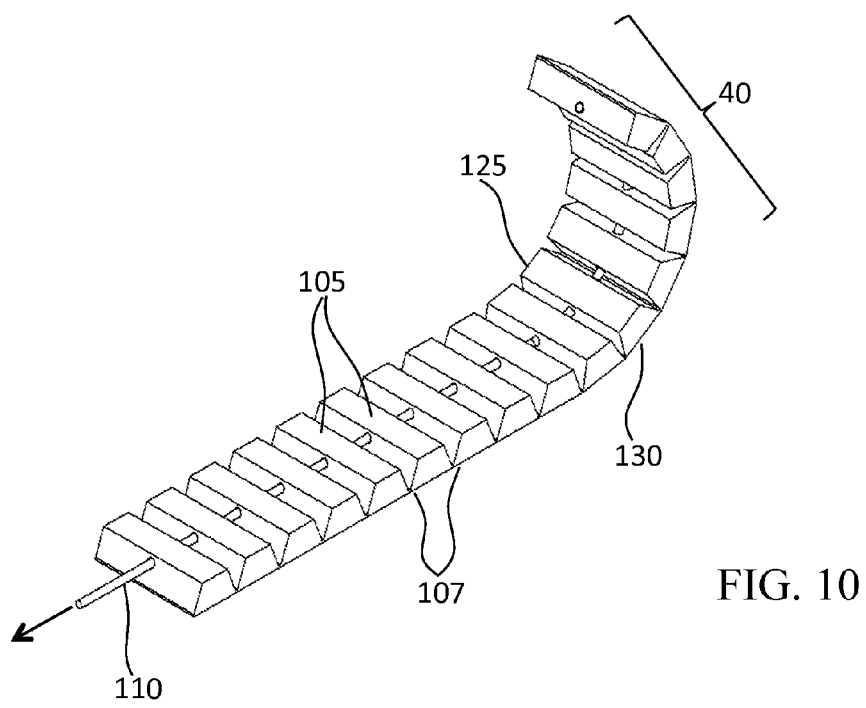
FIG. 10 is a perspective view of an extend-or-retract-to-engage embodiment of the articulating surface of the conforming arm that is retracted and engaged.
Figure 11:
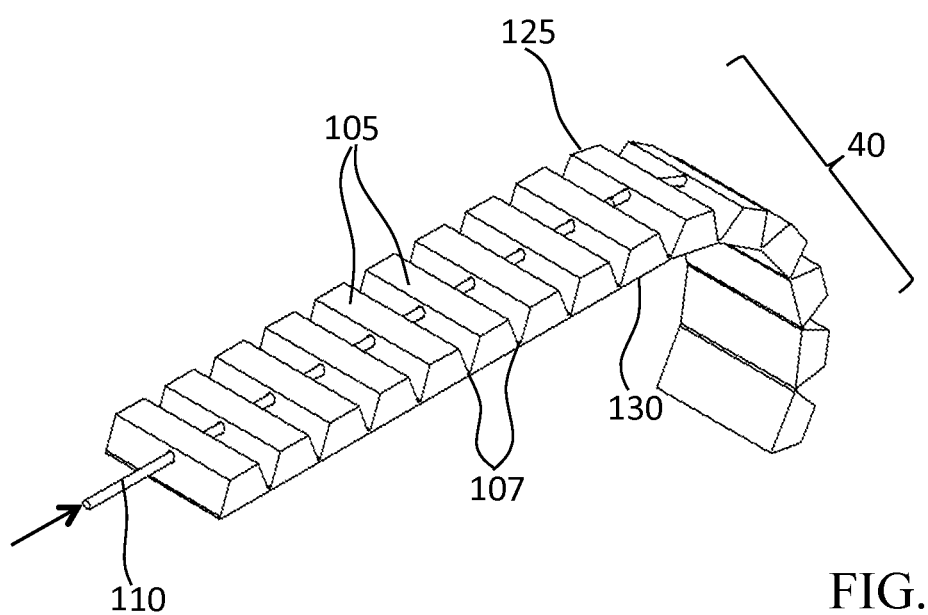
FIG. 11 is a perspective view of an extend-or-retract-to-engage embodiment of the articulating surface of the conforming arm that is extended and reverse-flexed.

In FIG. 9, there is shown the actuating surface 40 that is engaged by extending or retracting the actuator 110. The actuating surface 40 is made up of a series of segments 105 that are flexibly connected by a series of hinges 107. The actuator 110 passes through or is otherwise maintained in slidable contact with each individual segment 105. When the actuator 110 is extended or contracted, the series of segments begins to bend at the series of hinges 107. The pressure created by the actuator 110 retracting causes the series of segments 105 to bend, as shown in FIG. 10. Retracting the actuator 110 causes the non-hinged edge 125 of each individual segment to pivot or bend toward from the immediately adjacent segment. In FIG. 11 it is shown that extending the actuator 110 causes the non-hinged edge 125 of each individual segment to pivot or bend away from the immediately adjacent segment. As the actuator 110 continues to extend or retract, the actuating surface 40 will cause the conforming arm 20 to conform to the object either above or below the actuating surface 40 and begin to exert a grasping force against the perimeter of the object 22.

The actuating surface 40 shown in FIGS. 9-11 is capable of active reverse flexing, or bending away from the object. In one embodiment, the patient support surface 10 is positioned on top of an existing operating table or transport bed. The conforming arms 20 extend laterally past the edge of the support table. The actuating surface 40 is capable of reverse flexing, which causes the conforming arms 20 to bend outwardly such that the conforming arms 20 drape over the edge of the table and curve underneath the table. This unengaged position reduces the perimeter of the support surface 10, thereby providing more intimate access to the un-grasped object or patient by persons or equipment is useful for storage and the initial positioning of the patient or the object.

In one embodiment, the conforming arm is resistant to reverse-flexing from the flat non-engaged state. A conforming arm 20 design that is resistant to reverse-flexing provides a temporary rigid secondary support understructure, especially when used on a generally horizontal surface where the segmental elements might overhang the boundaries of the main understructure. This would provide a larger initial support surface 10. Once engaged, that surface would grasp the object 22, reducing the perimeter of the support surface 10, thereby providing more intimate access to the grasped object or patient by persons or equipment.

Figure 12:
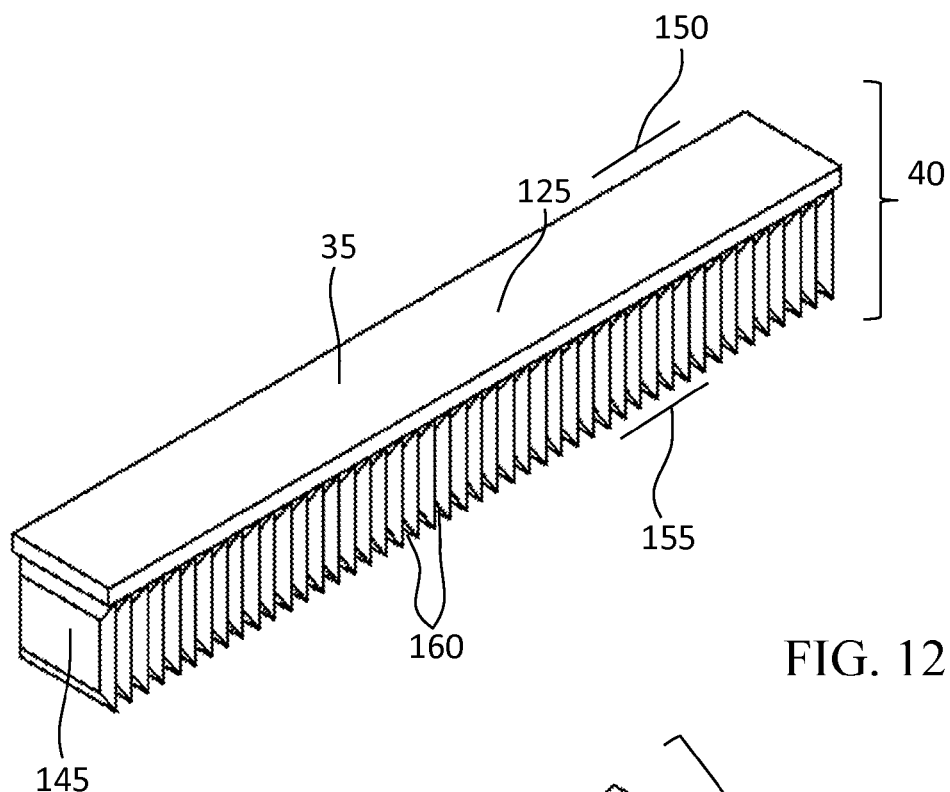
FIG. 12 is a perspective view of a bellows embodiment of the unengaged articulating surface of the conforming arm.
Figure 13:
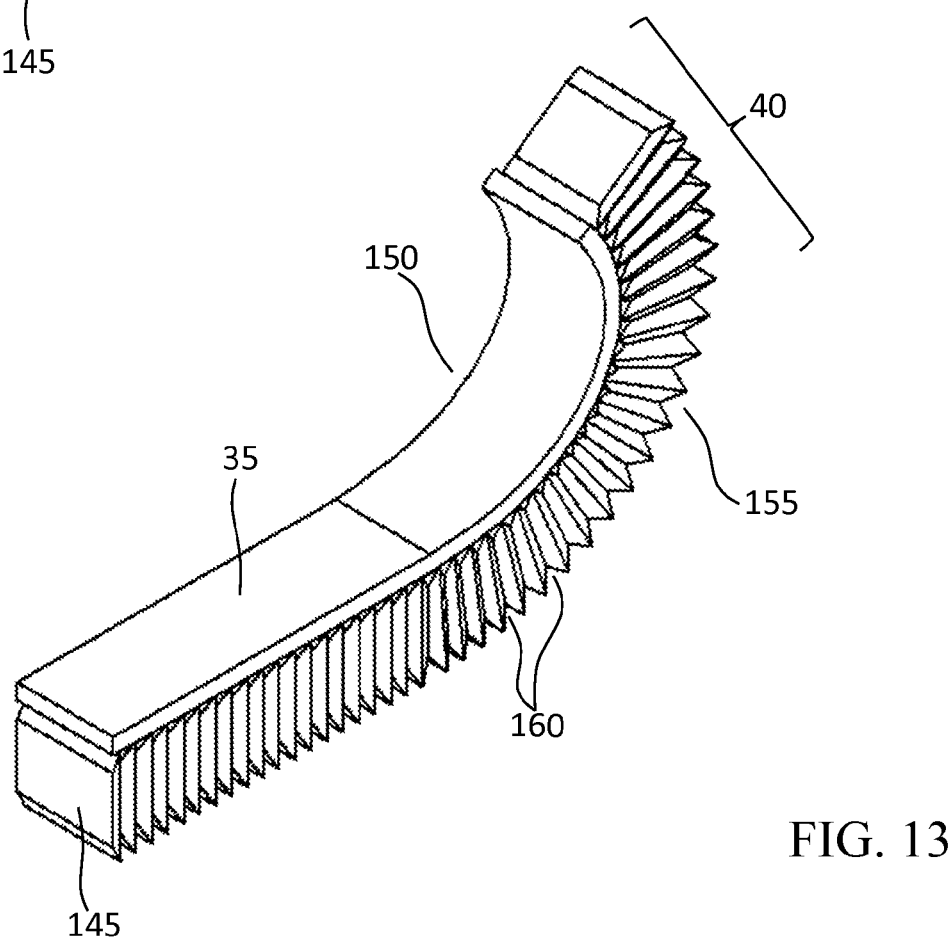
FIG. 13 is a perspective view of a bellows embodiment of the engaged articulating surface of the conforming arm.

In another embodiment shown in FIG. 12, the actuating surface 40 can utilize a bellows 145, which can be an accordion-type convoluted or corrugated hollow body or vessel. The bellows has a non-expanding surface 150 and an expanding surface 155 and. The non-expanding surface 150 of the bellows is attached to the non-elastic object contact surface 35, which prevents the non-expanding surface 150 from expanding. The bellows folds 160 acts as a hinge to enable extension during energization and retraction during de-energization. The bellows 145 are activated using a mechanical or fluid actuation.

In another embodiment, the actuating surface 40 is made up of a pneumatic or hydraulic actuator as described in the following U.S. Pat. No. 3,924,519 to England and U.S. Pat. No. 7,331,273 to Kerekes, the disclosures of which are incorporated by reference. Briefly, these patents describe an actuating surface 40 that is capable of curving toward an object. The actuating surface 40 is flexible with one or more flexible pressure ducts. The flexible pressure ducts are arranged to produce tangential forces when pressurized, thereby causing the actuating surface 40 to bend toward the object.

The action of the actuator 110 can be operator-generated, mechanically-generated, electronically-generated, or programmatically generated and transmitted by any effective means, such as via cable, rope, strap, or other linear actuator or force transmitter. The conforming action can also be generated by fluid power, such as hydraulic, pneumatic, or other energizing force that is in communication with the conforming arm.

A control system 24, as seen in FIG. 1, controls the engagement of the conforming arms 20. In one embodiment, the control system controls the activation of individual actuators 110. Each actuator 110 controls the engagement state of the individual conforming arms 20. Controlling individual actuators 110 allows the control system 24 to selectively engage non-fragile areas 25 and avoid exerting grasping force on fragile areas 30.

The control system 24 can engage and disengage individual conforming arms to alternate the grasping force pressure on specific portions of the object. Controlling individual actuators 110 also allows the control system to alternate the pressure contact areas to reduce and prevent damage from prolonged pressure. In the case of a human body, alternating the activation state of individual conforming arms can prevent trauma from the prolonged grasping force.

In another embodiment, the control system 24 regulates the degree or the extent of grasping pressure applied to the fragile areas 30 distinct from the non-fragile areas 25. Therefore the control system 24 can cause an individual conforming arm 20 to grasp a less fragile area 25 with a greater grasping force than another individual conforming arm 20 grasps a more fragile area 30.

Additionally, the support system 10 can maintain a desired object or patient core body temperature by pumping temperature regulated fluid, such as heating or cooling fluids, within the object conforming arms. Alternatively, resistive heating or piezoelectric heating/cooling may be implemented. The intimate contact of the conforming arms around the perimeter of the object facilitates rapid heat transfer. The control system can monitor the temperature of the object and pump fluid for heating or cooling the object to maintain the desired temperature.

Figure 14:
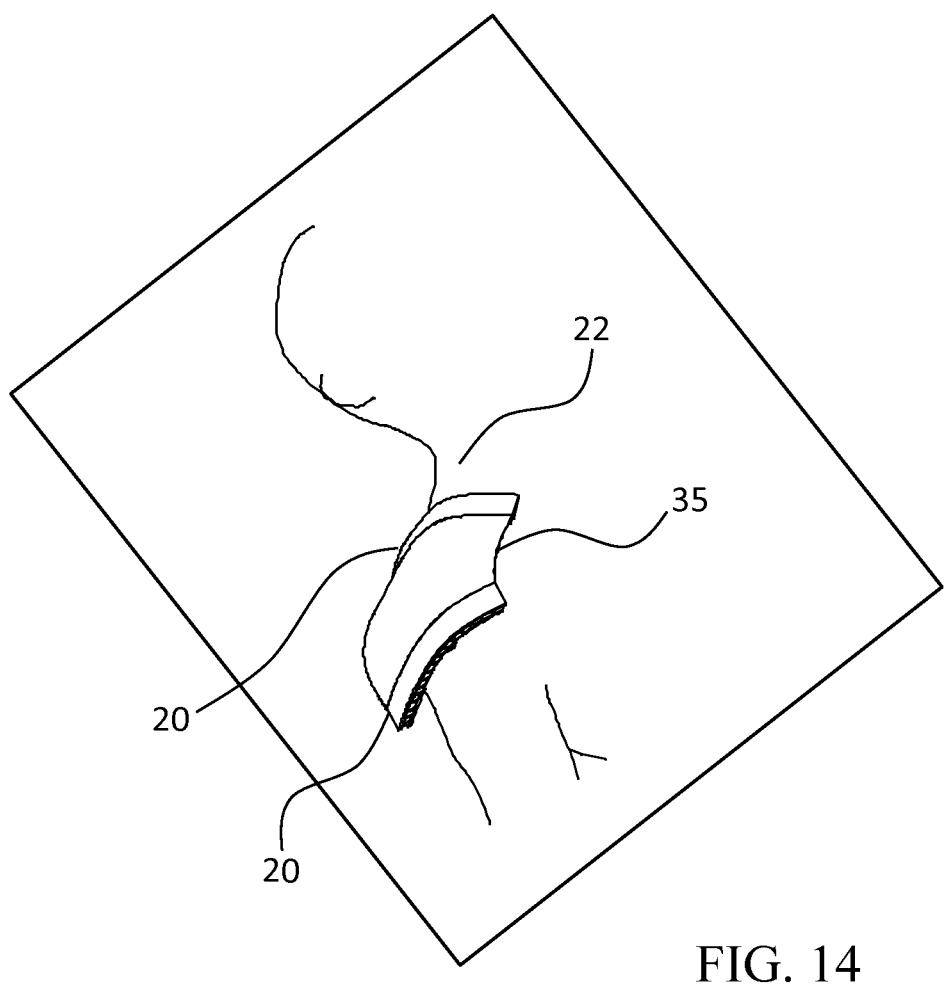
FIG. 14 is a perspective view an embodiment of the support surface where the object contact surface extends between a pair of conforming arm.

In FIG. 14, there is shown an embodiment where the object contact surface 35 spans between two conforming arms 20. In this embodiment, the object contact surface 35 engages a greater surface area of the object, thereby spreading the gripping force. Further, by utilizing an object contact surface material that is semi-elastic, the object contact surface will conform to irregular shaped areas of the object 22, such as the shoulder of a human body as illustrated.

Figure 15:
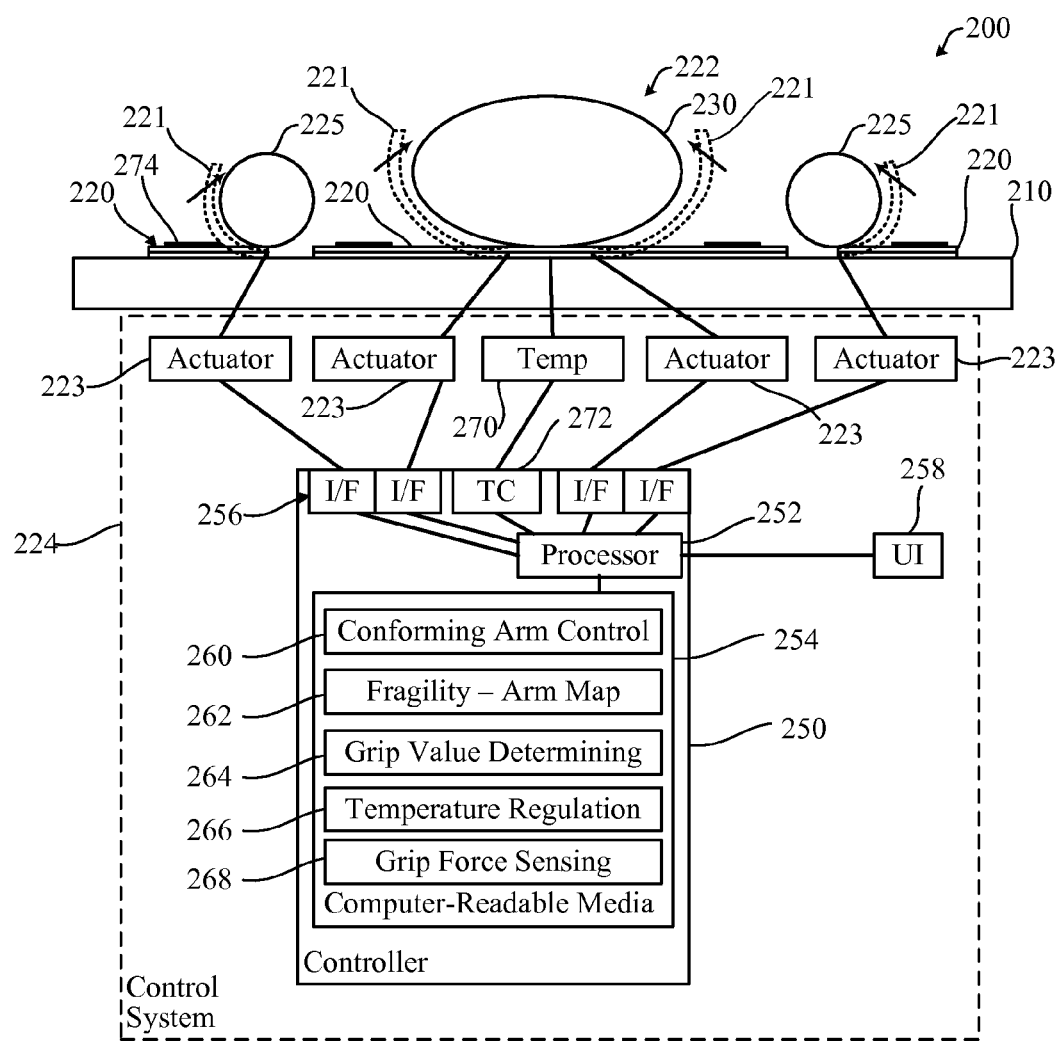
FIG. 15 is a side view in cross section of the disengaged support system of FIG. 1, with the engaged conforming arms depicted in phantom, and a block diagram of the control system.

In FIG. 15, an apparatus 200 is depicted for securing an object 222 that is partially fragile, composed of less fragile areas 225 and more fragile areas 230. A plurality of conforming arms 220 each respectively may be attached to a support surface 210 in a pattern for cooperatively receiving the object 222. Each arm 220 may have a conforming portion 221 that selectively curves inwardly. A plurality of actuators 223 respectively position the plurality of conforming arms 220 between a disengaged state to receive the object 222 and an engaged state (depicted in phantom) to contact the object 222 at a respective contact area to immobilize the object 222. A control system 224 selectively controls each of the plurality of actuators 223 to cause the respective one of the plurality of conforming arms to curve inwardly toward the object to cooperatively exert a grasping force upon the object such that only a fraction of total force required to immobilize the object is applied to the object by each individual conforming arm. A selected grasping force of a selected one of the plurality of conforming arm corresponds to a relative fragility of the respective contact area.

It should be appreciated with the benefit of the present disclosure that for clarity FIG. 15 depicts three (3) conforming arms 220, wherein exemplary implementations may have any number of conforming arms 220. Further, conforming arms 220 may be attached to the support surface 210 at one end or in the center of the conforming arm 220. More than one actuator 223 may actuate each conforming arm 220, for example to independently actuate each end of center-attached conforming arm. For another example, additional grasping force may be achieved by cooperating actuators 223. For an additional example, different actuators 223 may achieve engagement and disengagement.

As an alternative to independently actuating each conforming arm 220, an actuator 223 may actuate more than one conforming arm 220. For example, conforming arms 220 assigned to more fragile areas 230 may be actuated by an actuator 223 having a lower power rating than the actuator that actuated conforming arms 220 assigned to less fragile areas 230. For example, a pneumatic or fluid source of a selected regulated pressure may actuate more than one conforming arm 220.

It should be appreciated that the control system 224 may be an analog system that is preconfigured to achieve selected grasping forces. For instance, the control system 224 may be a fluidic control device.

In an exemplary version, the control system 224 has an electronic controller 250 that controls the actuators 223. To that end, the electronic controller 250 has a processor 252 that accesses a computer-readable medium 254 to perform operations by the actuators 223 via one or more actuator interfaces/drivers 256 of:

responding to a user input on a user interface (UI) 258 to immobilize an object 222 on a support surface 210 by associating a relative fragility of a contact area of an object 222 on the support surface 210 with a corresponding conforming arm 220 of more than one conforming arm attached to the support surface; and selectively actuating the more than one conforming arm to inwardly curve in cooperative opposition to engage and immobilize the object, wherein the selectively actuating creates a selected grasping force of a selected one of the more than one conforming arm that corresponds to a relative fragility of the respective contact area.

To that end, the computer-readable medium may contain a conforming arm control application 260, a fragility-to-arm mapping data structure 262, a grip value determining calculator 264, a temperature regulation application 266, and a grip force sensing utility 268.

In one aspect, the plurality of conforming arms 220 is disposed in a pattern that corresponds to the general perimeter of the object 222.

In another aspect, a size of the selected conforming arm 220 corresponds to the relative fragility to achieve the selected grasping force.

In one aspect a selected power rating of a selected one of the plurality of actuator 223 corresponds to the relative fragility to achieve the selected grasping force.

In an additional aspect, the control system 224 selectively commands a value to a respective one of the plurality of actuators 223 that corresponds to the relative fragility to achieve the selected grasping force. In an exemplary aspect, the control system 224 selectively commands the value that is inversely proportional to the relative fragility of the respective contact area.

In a further aspect, the control system 224 selectively commands a respective one of the plurality of actuators 231 based on the relative fragility of the respective contact area by selectively activating individual conforming arms that contact the object in a less fragile area.

In one aspect the control system 224 alternates the activation state of the plurality conforming arms 220 such that continuous pressure is not exerted on a single contact area of the object 222.

In another aspect, a temperature regulator 270 may be connected to the plurality of conforming arms. In an exemplary aspect, the temperature regulator may be a fluid conduit connected to a source for temperature regulated fluid to affect a temperature of the object by regulating a flow of the temperature regulated fluid through the plurality of conforming arms. Alternatively, the temperature regulator may be an electrical temperature regulator. In an exemplary aspect, the electronic controller 250 may have a temperature control interface 272 for controlling the temperature regulator 270.

In a particular aspect, each of the plurality of conforming arms 220 may have a contact surface 235 and an actuator surface 240, wherein the contact surface 235 may be laterally flexible and longitudinally inelastic, and wherein the actuator surface 240 may be a longitudinally inelastic lateral side connected to the contact surface 235 and comprises a longitudinally expandable lateral side. For example, the actuators 223 may be extend-to-engage actuators. Alternatively or in addition, the actuators 223 may be retract-to-engage actuators. Alternatively or in addition, the plurality of actuators 223 may be pneumatic actuators. Alternatively or in addition, the plurality of actuators 223 may be baffle actuators.

The actuator 223 may provide one or more sources of motive power to cause the actuating surface 240 to extend or retract. For example, an electrical linear motor, electrical stepper motor, an electric solenoid, etc., may act upon by pulling or pushing an actuator 110 (FIG. 5 6). Alternatively, the actuator 223 may be a piston that is pneumatic, fluidically, or hydraulically positioned to act upon an actuator 110.

In certain implementations, at least two of the conforming arms 220 are spaced apart for parallel inward curving movement to position a conforming, semi-elastic surface attached there between to an irregularly shaped portion of the object (FIG. 14).

In one aspect, at least one of the plurality of conforming arms forms a horizontal rigid structure to a downward force when in a disengaged state.

In another aspect, an apparatus secures an object that is partially fragile, composed of less fragile areas and more fragile areas. Conforming arms each have a contacting surface 235 and an actuating surface 240 and each respectively are attachable to a support surface 210 in a pattern for cooperatively receiving an object 222. A plurality of actuators respectively position the plurality of conforming arms by selectively expanding and retracting the actuating surface to inwardly curve the contacting surface 235 between a disengaged state to receive the object 222 and an engaged state to contact the object 222 at a respective contact area to immobilize the object 222. A control system 224 that dynamically controls each of the plurality of actuators to cause the respective one of the plurality of conforming arms to curve inwardly toward the object to cooperatively exert a grasping force upon the object such that the object is immobilized and the more fragile areas are not damaged.

In an exemplary aspect, a pressure transducer 274 positioned to sense the grasping force. The control system 224 is responsive to the pressure transducer 274.

Figure 16:
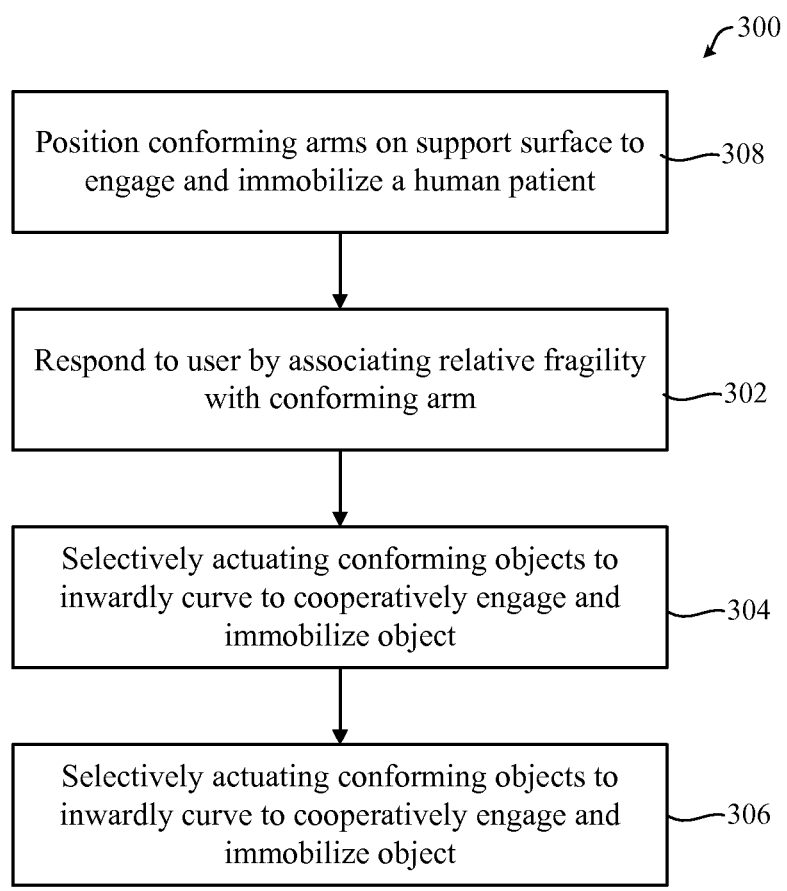
FIG. 16 is a flow diagram of a method of supporting an object with conforming arms.

In FIG. 16 according to one aspect, a method 300 is depicted for securing an object that is composed of a less fragile area and a more fragile area. An object immobilizing apparatus responds to a user input on a user interface to immobilize an object on a support surface by associating a relative fragility of a contact area of an object on the support surface with a corresponding conforming arm of more than one conforming arm attached to the support surface (block 302). The object immobilizing apparatus selectively actuates the more than one conforming arm to inwardly curve in cooperative opposition to engage and immobilize the object (block 304). The object immobilizing apparatus creates a selected grasping force of a selected one of the more than one conforming arm that corresponds to a relative fragility of the respective contact area (block 306).

In an exemplary aspect, the more than one conforming arms are positioned on the support surface to engage and immobilize a human patient (block 308).

While the foregoing disclosure discusses illustrative aspects and/or embodiments, it should be noted that various changes and modifications could be made herein without departing from the scope of the described aspects and/or embodiments as defined by the appended claims. Furthermore, although elements of the described aspects and/or embodiments may be described or claimed in the singular, the plural is contemplated unless limitation to the singular is explicitly stated. Additionally, all or a portion of any aspect and/or embodiment may be utilized with all or a portion of any other aspect and/or embodiment, unless stated otherwise.

It should be appreciated that any patent, publication, or other disclosure material, in whole or in part, that is the to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is the to be incorporated by reference herein, but which conflicts with existing definitions, statements, or other disclosure material set forth herein, will only be incorporated to the extent that no conflict arises between that incorporated material and the existing disclosure material.

What is claimed is:

1. An apparatus for securing an object that is partially fragile, composed of less fragile areas and more fragile areas, comprising:
   a. a plurality of conforming arms, each comprising a contacting surface and an actuating surface and each respectively attachable to a support surface in a pattern for cooperatively receiving an object;
   b. a plurality of actuators that respectively position the plurality of conforming arms by selectively expanding and retracting the actuating surface to inwardly curve the contacting surface between a disengaged state to receive the object and an engaged state to contact the object at a respective contact area to immobilize the object; and
   c. a control system that dynamically controls each of the plurality of actuators to cause the respective one of the plurality of conforming arms to curve inwardly toward the object to cooperatively exert a grasping force upon the object such that the object is immobilized and the more fragile areas are not damaged.

2. The apparatus of claim 1, wherein the actuating surface is expandable.

3. The apparatus of claim 1, wherein a size of a selected conforming arm corresponds to the relative fragility to achieve the selected grasping force.

4. The apparatus of claim 1, wherein a selected power rating of a selected one of the plurality of actuator corresponds to the relative fragility to achieve the selected grasping force.

5. The apparatus of claim 1, wherein the control system selectively commands a value to a respective one of the plurality of actuators that corresponds to the relative fragility to achieve the selected grasping force.

6. The apparatus of claim 1, wherein the control system selectively commands a respective one of the plurality of actuators based on the relative fragility of the respective contact area by selectively activating individual conforming arms that contact the object in a less fragile area.

7. The apparatus of claim 1, wherein the control system alternates an activations state of at least one of the plurality of conforming arms such that continuous pressure is not exerted on a single contact area of a portion of the object and while maintaining the portion of the object immobilized.

8. The apparatus of claim 1, further comprising a temperature regulator connected to the plurality of conforming arms.

9. The apparatus of claim 8, wherein the temperature regulator comprises a fluid conduit connected to a source for temperature regulated fluid to affect a temperature of the object by regulating a flow of the temperature regulated fluid through the plurality of conforming arms.

10. The apparatus of claim 8, wherein the temperature regulator comprises an electrical temperature regulator.

11. The apparatus of claim 1, further comprising a conforming, semi-elastic material attached between two of the plurality of conforming arms, wherein engaging the two conforming arms positions the material to conform to an irregularly shaped portion of the object.

12. The apparatus of claim 1, wherein at least one of the plurality of conforming arms is resistant to a downward force when in a disengaged state.

13. The apparatus of claim 1, further comprising a pressure transducer positioned to sense the grasping force, wherein the control system is responsive to the pressure transducer.

14. An apparatus for securing an object that is partially fragile, composed of less fragile areas and more fragile areas, comprising:
   a. a plurality of conforming arms, each comprising a contacting surface and an actuating surface and each respectively attachable to a support surface in a pattern for cooperatively receiving an object;
   b. a plurality of actuators that respectively position the plurality of conforming arms by selectively expanding and retracting the actuating surface to inwardly curve the contacting surface between a disengaged state to receive the object and an engaged state to contact the object at a respective contact area to immobilize the object;
   c. a control system that dynamically controls each of the plurality of actuators to cause the respective one of the plurality of conforming arms to curve inwardly toward the object to cooperatively exert a grasping force upon the object such that the object is immobilized and the more fragile areas are not damaged;
   d. wherein the control system selectively commands a value to a respective one of the plurality of actuators that corresponds to the relative fragility to achieve the selected grasping force; and
   e. wherein the control system selectively commands the value that is inversely proportional to the relative fragility of the respective contact area.

15. An apparatus for securing an object that is partially fragile, composed of less fragile areas and more fragile areas, comprising:
   a. a plurality of conforming arms, each comprising a contacting surface and an actuating surface and each respectively attachable to a support surface in a pattern for cooperatively receiving an object;
   b. a plurality of actuators that respectively position the plurality of conforming arms by selectively expanding and retracting the actuating surface to inwardly curve the contacting surface between a disengaged state to receive the object and an engaged state to contact the object at a respective contact area to immobilize the object;
   c. a control system that dynamically controls each of the plurality of actuators to cause the respective one of the plurality of conforming arms to curve inwardly toward the object to cooperatively exert a grasping force upon the object such that the object is immobilized and the more fragile areas are not damaged; and
   d. wherein the actuating surface has an expandable edge and a fixed length edge.

16. The apparatus of claim 15, wherein the plurality of actuators comprises a plurality of extend-to-engage actuators.

17. The apparatus of claim 15, wherein the plurality of actuators comprises a plurality of retract-to-engage actuators.

18. The apparatus of claim 15, wherein the plurality of actuators comprises a plurality of pneumatic actuators.

19. The apparatus of claim 15, wherein the plurality of actuators comprises a plurality of baffle actuators.

* * * * *